US006515018B1

(12) United States Patent
Fuhrman et al.

(10) Patent No.: US 6,515,018 B1
(45) Date of Patent: Feb. 4, 2003

(54) SYNERGISTIC COMPOSITIONS FOR LYCOPENE AND VITAMIN E FOR THE PREVENTION OF LDL OXIDATION

(75) Inventors: Bianca Fuhrman, Haifa (IL); Michael Aviram, Kiryat Haim (IL); Zohar Nir, Meitar (IL); Morris Zelkha, Omer (IL)

(73) Assignee: Lycored Natural Products Industries Ltd., Beer Sheva (IL)

( * ) Notice: Subject to any disclaimer, the term of this patent is extended or adjusted under 35 U.S.C. 154(b) by 0 days.

(21) Appl. No.: 09/446,241

(22) PCT Filed: Jun. 18, 1998

(86) PCT No.: PCT/IL98/00286

§ 371 (c)(1),
(2), (4) Date: Apr. 3, 2000

(87) PCT Pub. No.: WO98/57622

PCT Pub. Date: Dec. 23, 1998

(30) Foreign Application Priority Data

Jun. 19, 1997 (IL) .................................................. 121112

(51) Int. Cl.[7] ........................ A61K 31/355; A61K 35/78
(52) U.S. Cl. ........................................ 514/458; 424/727
(58) Field of Search ................................ 514/458, 762, 514/763, 824; 424/195.1, 777

(56) References Cited

U.S. PATENT DOCUMENTS 5,849,787 A * 12/1998 Fujiwara et al. ............ 514/458
5,871,766 A *  2/1999 Hennekens .................. 424/422

FOREIGN PATENT DOCUMENTS

| WO | 92 05780 | 4/1992 |
|---|---|---|
| WO | 95 35099 | 12/1995 |
| WO | 96 19215 | 7/1996 |
| WO | 96 19217 | 7/1996 |
| WO | 99 38518 | 5/1999 |

OTHER PUBLICATIONS

Haila et al., "Effects of Lutein, Lycopene, Annatto, and Tocopherol on Autoxidation of Triglycerides", *J. Agric Food Chem*, vol. 44, No. 8, pp. 2096–2100, (1996).

Wise et al., "Changes in Plasma Carotenoid, Alpha–Tocopherol, and Lipid peroxide Levels in Response to Supplementation with Concentrated Fruit and Vegetable Extracts: A pilot Study", *Current Therapeutic Research–Clinical and Experimental*, vol. 57, No. 6, pp. 445–461, (1996).

Woodall et al., "Caroteniods and protection of Phospholipids in solution or in liposomes against oxidation by peroxyl radicals: Relationship between carotenoid structure and protective ability", *Biochimica et Bipphysica Acta–General Subjects*, vol. 1336, No. 3, pp. 575–586, (1997).

Stahl et al., "Carotenoid mixtures protect multilamellar liposomes against oxidative damage: synergistic effects of lycopene and lutein", *FEBS Letters*, vol. 427, No. 2, pp. 305–308, (1998).

Fuhrman et al., "Tomato lycopene and β–carotene inhibit low density lipoprotein oxidation and this effect depends on the lipoprotein vitamin E content", *Nutr Metab Cariovasc Dis*, vol. 7, pp. 433–443, (1997).

Fuhrman et al., "Hypocholesterolemic Effect of Lycopene and βCarotene is Related to Suppression of Cholesterol Synthesis and Augmentation of LDL Receptor Activity in Macrophages", *Biochemical and Biophysical Research Communications*, vol. 233, pp. 658–662, (1997).

Hennekens et al., "Lack of Effect of Long–Term Supplementation with Beta Carotene on the Incidence of Malignant Neoplasma and Cardiovascular Disease", *The New England Journal of Medicine*, vol. 334, No. 18, pp. 1145–1149, (1996), Bohm et al., "Carotenoids protect against cell membrane damages by the nitrogen dioxide radical", *Nature Medicine*, vol. 1, No. 2, (1995).

Kohlmeier et al., "Epidemiologic evidence of role of carotenoids in cardiovascular disease prevention", *Am. J. Clin. Nutr.*, vol. 62, pp. 137S–146S, (1995).

Krinsky, "Antioxidant Functions of Carotenoids", *Free Radical Biology Medicine*, vol. 7, pp. 617–635, (1989).

Burton, "Antioxidant Action of Carotenoids", *J. Nutr.*, vol. 119, pp. 109–111, (1989).

Aviram, "Beyond Cholesterol: Modification of Lipoproteins and Increased Atherogenicity", *Scientific Press, Florence Italy*, pp. 15–36, (1993).

Witztum, "The oxidation hypothesis of atherosclerosis", *Lancet*, vol. 344, pp. 793–795, (1994).

Haberland et al., "The Role of altered lipoproteins in the pathogenesis of atherosclerosis", *New England Journal of Medicine*, vol. 113, No. 2, pp. 573–577, (1987).

Steinberg et al., "Beyond Cholesterol", *The New England Journal of Medicine*, vol. 320, No. 14, pp. 915–923, (1989).

Davies et al., "Atherosclerosis: what is it and why does it occur?", *Br. Heart J.*, vol. 69, pp. S3–S11, (1993).

Buege et al., "Microsomal Lipid Peroxidation", *Methods Enzymol*, vol. 52, pp. 302–310, (1978).

Dimascio et al., "Lycopene as the Most Efficient Biological Carotenoid Singlet Oxygen Quencher", *Archives of Biochemistry and Biophysical and Biophysical*, vol. 274, No. 2, pp. 532–538, (1989).

Castelli et al., "Lipids and Risk of Coronary Heart Disease The Framingham Study", *Ann. Epidemiol*, vol. 2, No. 1–2, pp. 23–28, (1992).

* cited by examiner

*Primary Examiner*—Theodore J. Criares
(74) *Attorney, Agent, or Firm*—Browdy and Neimark (57) ABSTRACT

A synergistic mixture containing lycopene and Vitamin E and its use in the prevention of LDL oxidation. Lycopene is either synthetic or from natural sources. Furthermore the preparation of a pharmaceutical and a dietary composition for arresting the progression of atheroclerosis is described.

22 Claims, 7 Drawing Sheets

FIG.1A
VITAMIN E INHIBITS COPPER IONS-INDUCED LDL OXIDATION

FIG.1B

FIG. 2A

LYCOPENE INHIBITS COPPER IONS-INDUCED LDL OXIDATION

FIG. 2B

FIG. 3A
LYC-O-MATO (6%) INHIBITS COPPER IONS-INDUCED LDL OXIDATION

FIG. 3B

FIG. 4A
LYC-O-MATO (DW) INHIBITS COPPER IONS-INDUCED LDL OXIDATION

FIG. 4B

FIG.5A

EFFECT OF A COMBINATION OF LYCOPENE AND VITAMIN E ON COPPER IONS-INDUCED LDL OXIDATION

EFFECT OF A COMBINATION OF LYC-O-MATO DW AND VITAMIN E ON COPPER IONS-INDUCED LDL OXIDATION

FIG. 7B

SYNERGISTIC COMPOSITIONS FOR LYCOPENE AND VITAMIN E FOR THE PREVENTION OF LDL OXIDATION

CROSS REFERENCE TO RELATED APPLICATION

The present application is the national stage under 35 U.S.C. 371 of PCT/IL98/00286, filed Jun. 18, 1998.

FIELD OF THE INVENTION

The present invention concerns a composition containing lycopene and Vitamin E.

This present invention more particularly relates to a synergistic mixture of lycopene and vitamin E and its use in the prevention of LDL oxidation, and preparing pharmaceutical and dietary compositions for arresting the progression of atheroclerosis.

BACKGROUND OF THE INVENTION

Atherosclerosis is the major single cause of mortality in western society. It is assumed to reach up to 50% of all mortality (Davies M J, and Woolf N. *Atherosclerosis: what is it and why does it occur? Br Heart J* 69:S3, 1993). In addition, it results in significant cardiac morbidity, such as anginal syndromes, myocardial infarctions, ischemic cardiomyopathy, sudden cardiac death, cerebrovascular accidents, and peripheral vascular disease. Indisputable evidence for an association between coronary heart disease (CHD) and risk factors, such as arterial hypertension, cigarette smoking and hyperlipidemia, has been derived from a variety of epidemiological studies. Of all the risk factors established thus far, lipid disorders play a key role in the pathogenesis of atherosclerotic vascular disease, especially of CHD. Many epidemiological and clinical trials have demonstrated the powerful association between hyperlipidemia and the widespread incidence of CHD. The Framingham Heart Study (Castelli W P, Anderson K, Wilson P W., Levy D. *Lipids and risk of coronary heart disease. The Framingham Study. Ann Epidemiol* 2(1–2): 23–28, 1992), which has been continuous since 1984, showed that hypercholesterolemia is a major contributor to the development of CHD. The link between atherosclerosis and cholesterol has been confirmed by a number of clinical trials.

Fats are insoluble in the aqueous medium of the blood. Thus, transport of the lipids triglycerides, phospholipids and cholesterol occurs exclusively by way of lipid-protein complexes, the lipoproteins. The lipoproteins are classified into 4 broad classes-chylomicrons, very low density lipoprotein (VLDL), low density lipoprotein (LDL), and high density lipoprotein (HDL), which differ in their composition, size, and potential atherogenicity.

Measurement of total cholesterol level in plasma reflects the sum of cholesterol being transported in each individual lipoprotein. However, LDL and HDL are the main cholesterol carriers in plasma, and only a small fraction of cholesterol is carried in VLDL or in the chylomicrons. Atherosclerosis is a gradual pathological process, which is characterized by an accumulation of lipid filled macrophages (foam cells), and smooth muscle cells resulting in lesions that thicken and harden the arterial wall. The main source for the cholesterol accumulating in the foam cells is the circulating LDL. There is evidence from numerous epidemiological and clinical studies that LDL, as the carrier of ca. 70% of the total cholesterol in plasma, are the most potent atherogenic lipoproteins. Their elevation carries a particular risk, and reduction in LDL cholesterol constitutes a diminished atherosclerotic risk. The Lipid Research Clinics Coronary Primary Prevention Trial (LRC-CPPT) had for the first time presented firm proof that in man, a lowering of LDL cholesterol level reduces the rate of myocardial infarcaiton and infarction mortality.

Nearly all cells, including macrophages, take up exogenous cholesterol via LDL-receptors. Increase in cell cholesterol content, however, results in down-regulation of LDL receptor number, thereby protecting cells from excessive accumulation of cholesterol by way of this pathway. It was shown that chemical or biological modification, including oxidation of LDL, results in increased uptake of the modified lipoprotein by way of other cell surface receptors, termed scavenger receptors. These receptors are present on macrophages and endothelial cells.

Oxidative modification of LDL is thought to play a causal role in atherosclerosis: (see e.g. Steinberg D., Parthasarathy S., Carew T. E., Khoo J. C. and Witztum J. L, "Beyond cholesterol: modifications of low-density lipoprotein that increase its atherogenicity", N. Engl. J. Med. 1989; 320: 915–924; Haberland M. E. and Fogelman A. M., "The role of altered lipoproteins in the pathogenesis of atherosclerosis", Am. Heart. J. 1987; 113: 573–577; and Witztum J. L., "The oxidation hypothesis of atherosclerosis", Lancet. 1994; 344, 793). It is believed, accordingly, that prevention of LDL oxidation by antioxidants may arrest the progression of atherosclerosis. Aviram M. Beyond cholesterol: Modification of lipoproteins and increased atherogenicity. In Atherosclerosis, inflammation and thrombosis (G. G. Neri Serneri, G. F. Gensini, R. Abbate and D. Prisco eds)-Scientific Press-Florence, Italy, pp: 15–36, 1993.

The ability to prevent the development of atherosclerotic lesions would have major implications for the public health. Thus using therapeutic agent with plural effects, such as lowering cholesterol and inhibiting oxidative modification, might have beneficial effects over other individual agent.

Carotenoids are colored pigments with lipophilic properties, widely distributed in fruits and vegetables, (e.g. β-carotene in carrots and lycopene in tomatoes) and possess some antioxidant properties: (see e.g. Burton G. W., "Antioxidant action of carotenoids," 1989; J. Nutr. 119:109–111 and Krinsky N. I., "Antioxidant functions of carotenoids", Free Radic. Biol. Med. 1989, 7: 617–635 (9–13)). Carotenoids are transported within circulating lipoproteins, and it was postulated that they participate in the protection of LDL from oxidative modification.

Carotenoids consumption was shown in previous epidemiological studies to be associated with reduced cardiovascular mortality (see e.g.: Kohlmeier L. and Hasting S. B., "Epidemiologic evidence of a role of carotenoids in cardiovascular disease prevention", Am. J. Clin. Nutr. 1995; 62: 137S–146S), although recent data did not demonstrate similar beneficial effect (see e.g.: Hennekens C. H., Buring J. E., Manson J. E., Stampfer M, Rosier B., Cook N. R., Belanger C., LaMotte F., Gaziano J. M., Ridker P. M., Willett W. and Peto R., "Lack of effect of long-term supplementation with beta carotene on the incidence of malignant neoplasms and cardiovascular disease", N. Engl. J. Med. 1996; 334: 1145–1149).

Reduced plasma lipid peroxidation was recently shown to be associated with increased consumption of tomatoes. Low levels of plasma carotenoids were shown to be associated with an increased risk of myocardial infarction, and recently it was demonstrated that the association between β-carotene and acute myocardial infarction depends on the polyunsaturated fatty acids status, and that feeding the all-trans isomer of β-carotene to cholesterol-fed rabbits attenuated the extent of their atherosclerosis, with no effect on LDL oxidizability ex vivo. Data on the ability of β-carotene supplementation in vitro or in vivo to protect LDL from oxidation are conflicting: some studies found an inhibitory effect of β-carotene supplementation on LDL oxidation, whereas several other did not find such effect.

Lycopene, the open chain analog of β-carotene, shares with it similar structure with an extended conjugated double bonds. In human plasma, lycopene and β-carotene are quantitatively the major carotenoids. Lycopene was shown to possess the greatest quenching ability of singlet oxygen among the various carotenoids (DiMascio P., Kaiser S. & Sies H., "Lycopene as the most efficient biological carotenoid singlet oxygen quencher," Arch. Biochem. Biophys., 1989, 274: 532–538) and it was shown to be at least twice as effective antioxidant as β-carotene in protecting blood lymphocytes form $NO_2$ radical damage (Bohm F., Tinkler J. H., and Truscott T. G., "Carotenoids protect against cell membrane damage by the nitrogen dioxide radical", Nature Medicine, 1995, 2: 98–99).

We have recently demonstrated a protective effect of tomatoes lycopene against oxidative modification of LDL. This protection of LDL by lycopene exceeds the protection exhibited by β-carotene, was selective only to LDL's with high vitamin E content and was shown when the carotene was present in combination with vitamin E. (see e.g., Fuhrman B, Ben Yaish L, Attias J. Hayek T. Aviram M. *Tomatoes lycopene and β-carotene inhibit low density lipoprotein oxidation and this effect depends on the lipoprotein vitamin E. content.* Nutr Metab. Cardiovasc. Dis 7: 433–443, 1997). Furthermore, we have also demonstrated that dietary supplementation of lycopene acts as moderate hypocholesterolemic agent secondary to its inhibitory effect on cellular cholesterol syntheses (see e.g. Fuhrman B., Elis A., Aviram M., *Hypocholesterolemic effect of lycopene and β-carotene is related to suppression of cholesterol synthesis and augmentation of LDL receptor activity in macrophages.* Bichem. Biophys. Res. Commun. 233: (658–662, 1997).

Israel Patent Application No. 123,132 recently filed covers the use of a mixture of lycopene and garlic to be used in preventing LDL oxidation.

OBJECTIVES

It is an objective of the present invention to provide a novel mixture of lycopene and vitamin E. It is an objective of the present invention to provide a synergistic mixture of lycopene and vitamin E active in blocking the oxidation of LDL and/or atherosclerosis and reduce the cholesterol levels in plasma. An additional objective of the present invention is the use of the above described mixture to prepare a pharmaceutical or dietary composition for arresting the progression of atherosclerosis. A further objective of the present invention is to provide a composition for the arresting of the progression of atherosclerosis containing essentially products acceptable and desertable of the harm diet.

SUMMARY OF THE INVENTION

The invention is based on the discovery that there is an unexpected and surprising synergistic effect between lycopene and vitamin E, in the prevention of LDL oxidation. Lycopene is a natural product and is present in tomatoes in various concentrations, but can also be produced by fungal, algal or by fermentation, in genetically modified organisms (GMO) or by synthetic method. Compositions comprising it and their use are comprised in the present invention. A widely used source of vitamin E is soybean distillate.

The invention therefore provides a composition which is a combination of lycopene and vitamin E.

The composition may contain other dietary components, additives, excipients, binding agents, coatings, etc., or other compounds that have no significant effect in preventing LDL oxidation. The compositions according to the invention, in view of their purpose, are pharmaceutical compositions. However, since their components are individually acceptable ingredients of the human diet, and in fact are individually present in foodstuffs, they may be considered and used as dietary or health supplements.

The use of the aforesaid combinations of compounds as medicines or components of pharmaceutical compositions or of dietary or health compositions for the prevention of LDL oxidation is also an aspect of the present invention.

The use of tomato oleoresin for the prevention of LDL oxidation is a specific aspect of the present invention.

The compositions according to the invention should preferably comprise lycopene and vitamin E in a molar proportion of 1:400 to 10:1, preferably 1:80 to 5:1. The amount of lycopene in each unit of the composition, e.g. a tablet or soft gel capsule, should be in the range of 1–4, preferably about 2–3 and up to 15 mg of lycopene.

The invention comprises a method of preventing LDL oxidation, and therefore arresting the progression of atherosclerosis, which comprises administering to a patient lycopene and vitamin E, in the aforesaid relative amounts.

DETAILED DESCRIPTION OF PREFERRED EMBODIMENTS

In a preferred way of carrying out the invention, and in the Examples that will be described, lycopene was obtained from tomato oleoresin. The oleoresin was supplied by LycoRed-Natural Products Industries, Ltd, Beer Sheva, Israel. It consisted of crystalline lycopene (6.0%) suspended in the lipid phase of the tomato. Fatty acids as triglycerides constituted the major part (72%) of the oleoresin, whereas 19% were non-saponified materials including 6.0% lycopene, 0.1% β-carotene and 1% vitamin E. The rest consists of water and water soluble materials. The lycopene used was extracted and purified mainly in the all-trans configuration. Lycopene can be extracted from tomato oleoresin, as described in Patent Application No. WO 97/48287.

Vitamin E is readily available in the pharmaceutical market.

Said ingredients are conveniently available and used in the form of oleoresin or in a solid form such as beadlets.

Materials

Supplementation of Human LDL with Lycopene

Stock solutions of 1 mM of purified lycopene or of 10 mg/ml of tomato's oleoresin, were prepared in Tetrahydrofuran (THF, HPLC grade). All procedures were performed in dim light. LDL was incubated with the respective concentrations of tomato's oleoresin or with 3 μM of lycopene (3 μl/ml THF, derived from a stock solution of 1 mM) for 30 minutes at 37° C. in the dark. LDL incubated with THF alone served as control.

LDL Oxidation

Oxidation of LDL was carried out in a shaking water bath at 37° C. under air, in plastic tubes (1 cm in diameter). For metal ions dependent oxidation LDL was incubated for 4 hours at 37° C. with freshly prepared $CuSO_4$ (5 μM).

LDL oxidation was determined by measuring the amount of thiobarbituric acid reactive substances (TBARS) (See: Buege J. A. and Aust S. D. Microsomal lipid peroxidation. Methods Enzymol. 1978; 52: 302–310) and by lipid peroxides formation using a commercially available kit.

Effects of Lycopene or Vitamin E Alone Against LDL Oxidation

Figure 1A:
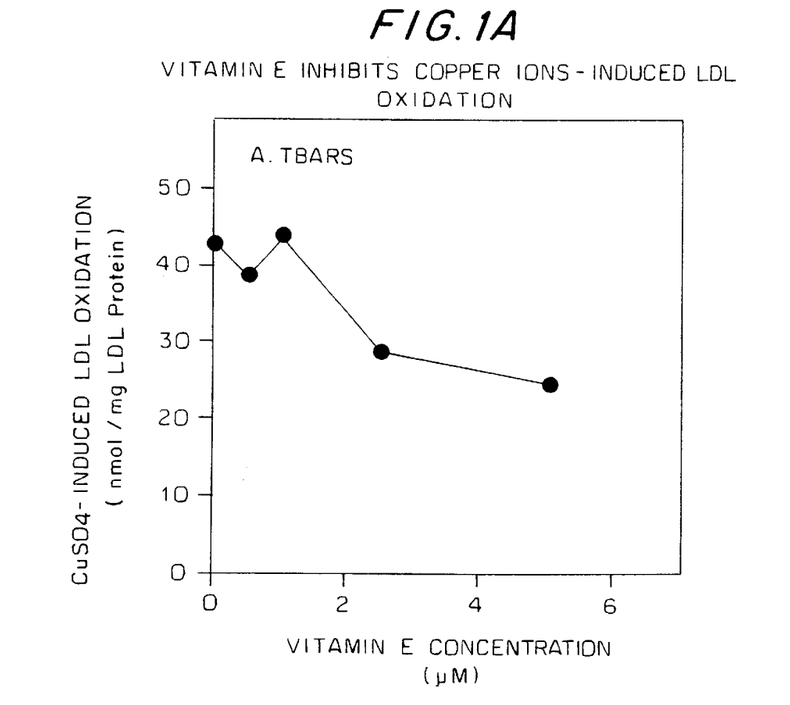
Figure 1B:
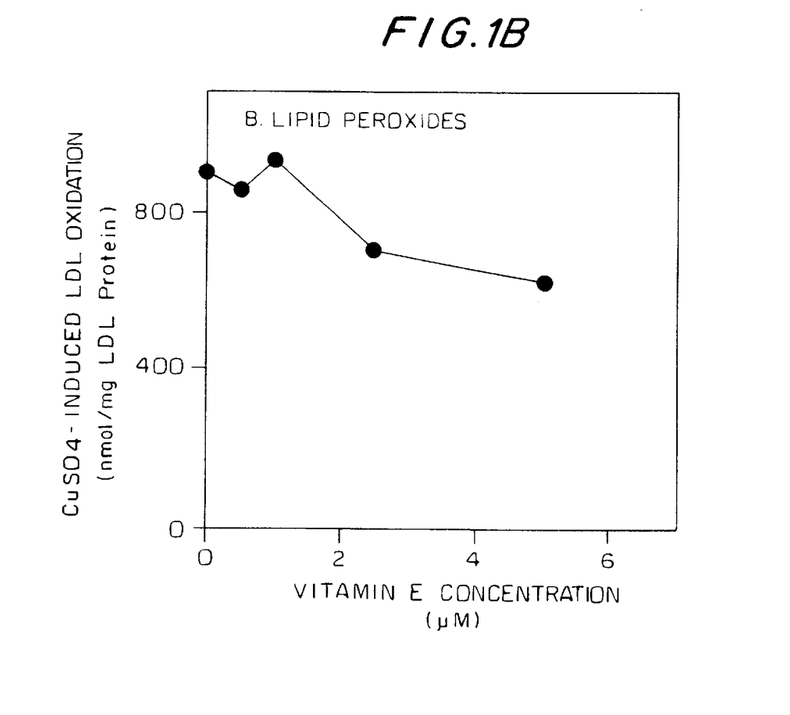
Figure 3A:
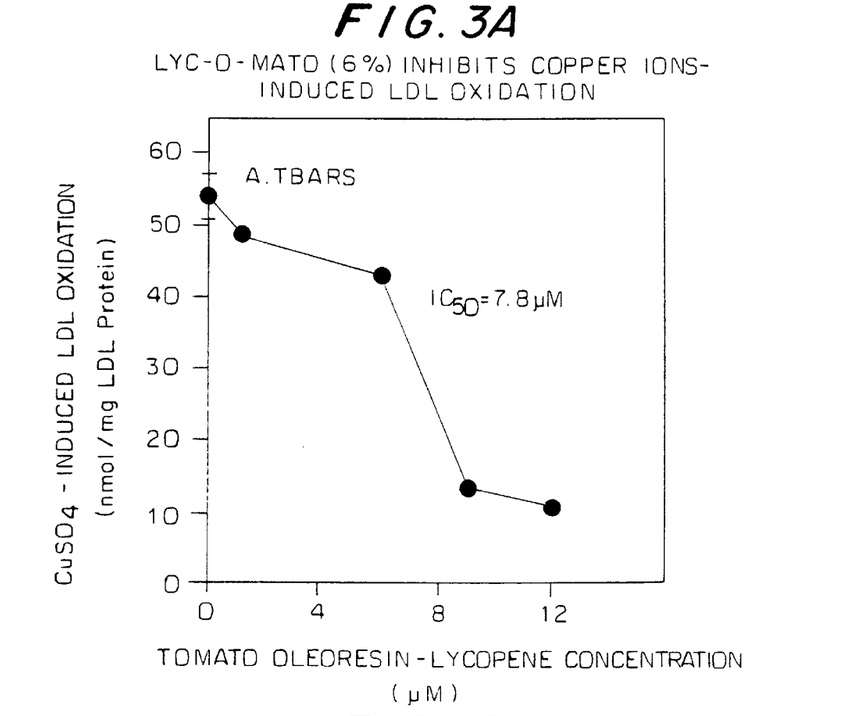
Figure 3B:
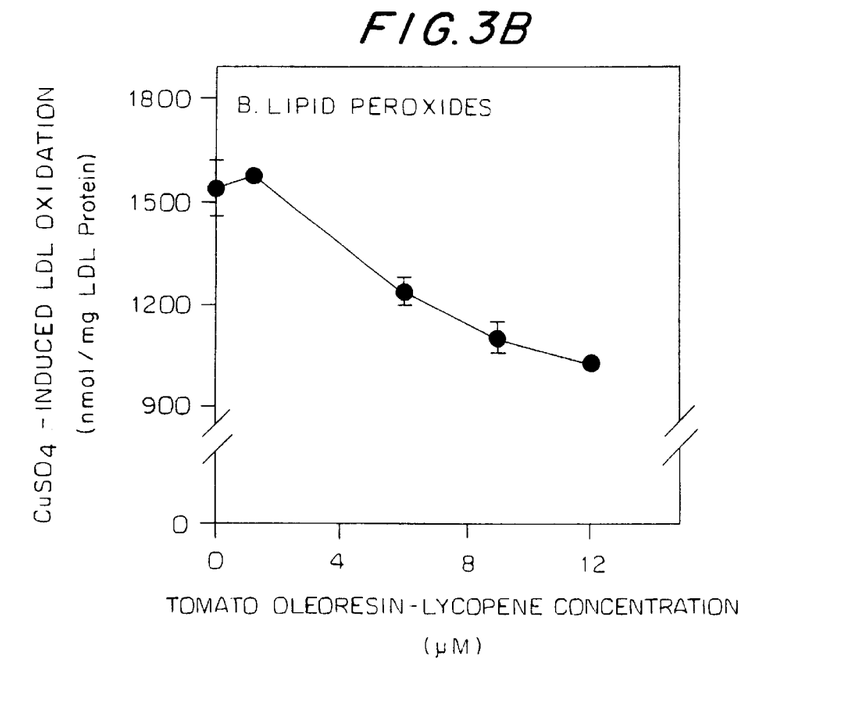
Figure 4A:
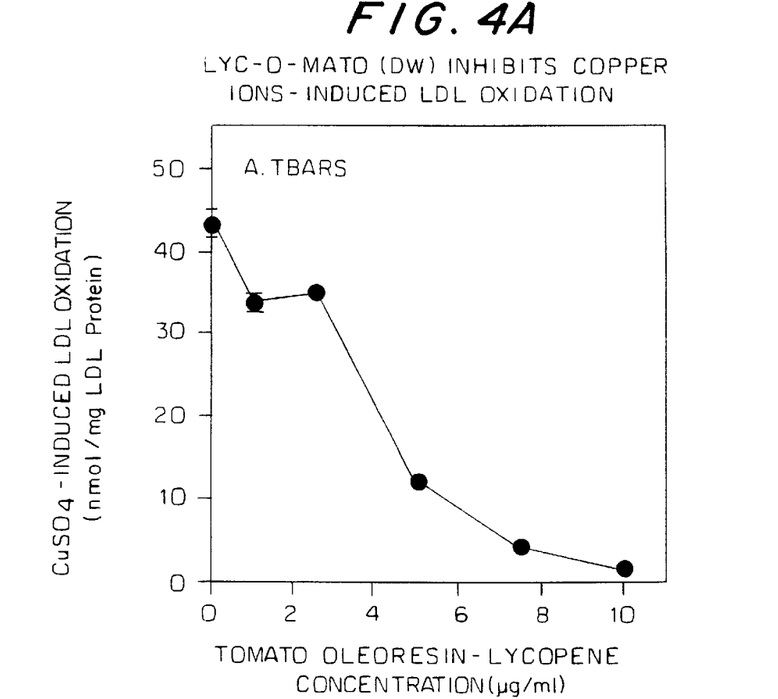
Figure 4B:
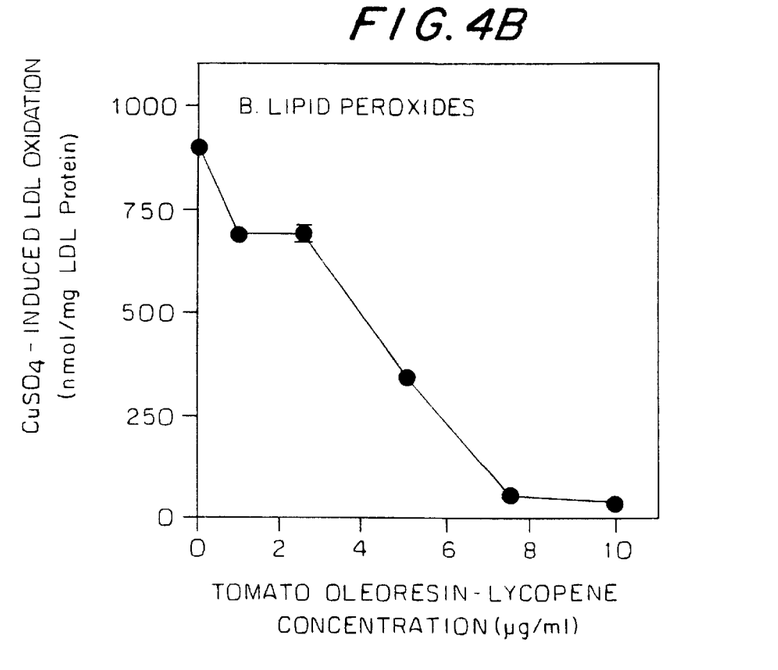

LDL (100 μg of protein/ml) was preincubated for 30 min at 37° C. with either vitamin E or lycopene in various forms. LDL oxidation was induced by the addition of 5 μM of $CuSO_4$ and was preincubated for 30 min at 37° C. LDL oxidaton was measured by the TBARS assay or by measuring the inhibition of the formation of lipid peroxides. Results are shown in FIG. 1 for vitamin E inhibition and FIG. 2 for crystalline lycopene. FIG. 3 shows the effect for tomato oleoresin, and for comparison, FIG. 4 shows the results for tomato oleoresin where the natural occurring vitamin E was extracted out.

Effect of Lycopene in Combination With Vitamin E Against LDL Oxidation

Figure 5A:
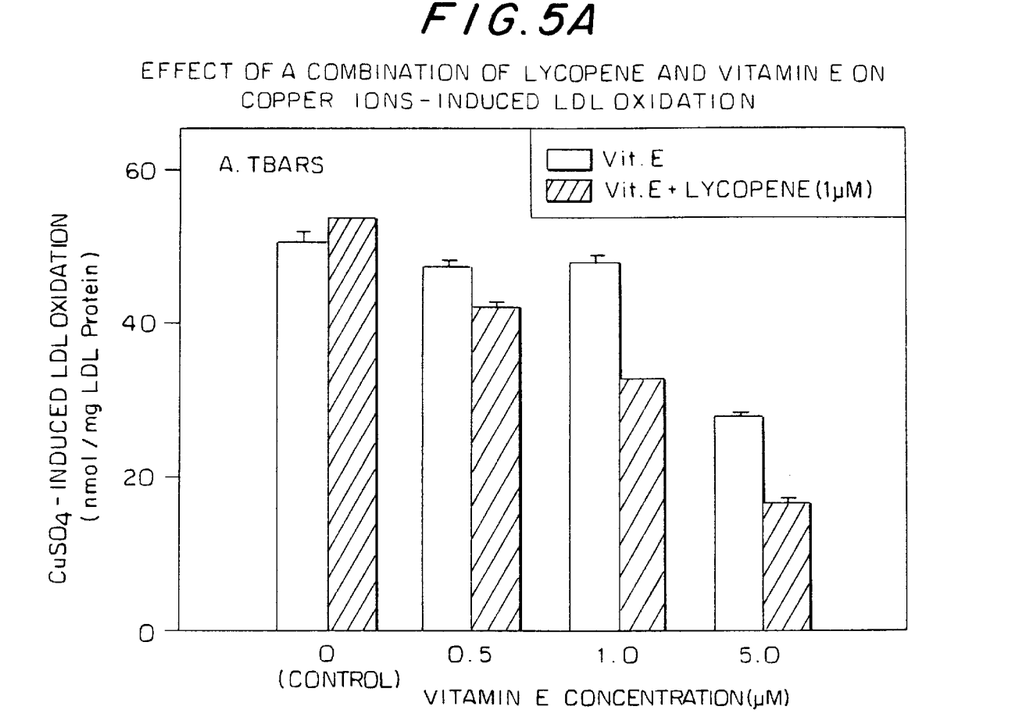
Figure 5B:
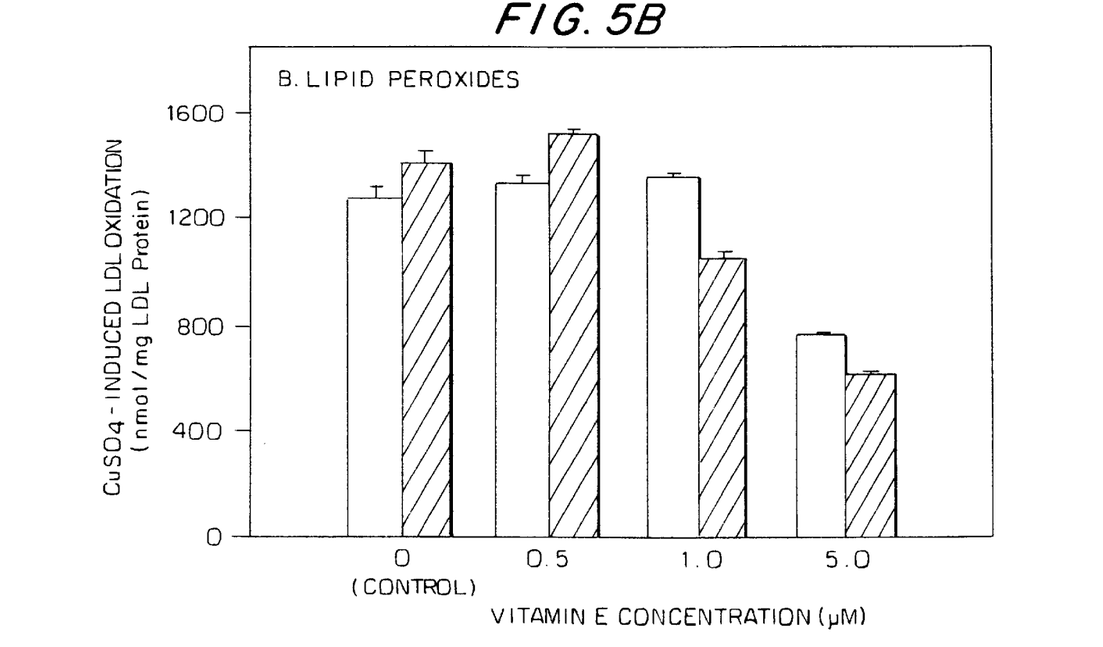
Figure 6A:
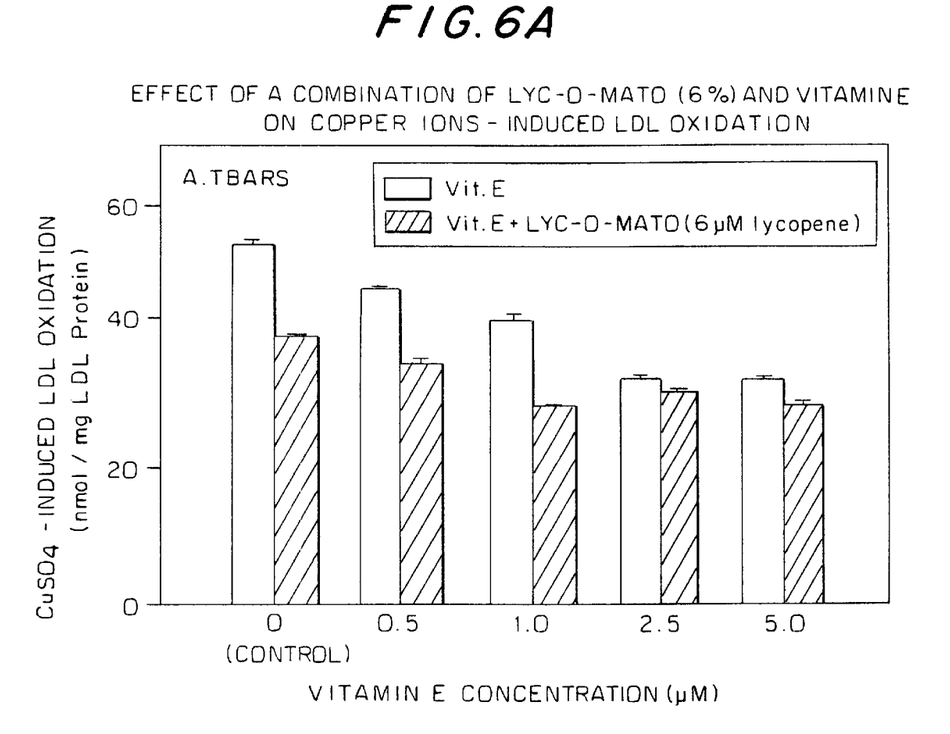
Figure 6B:
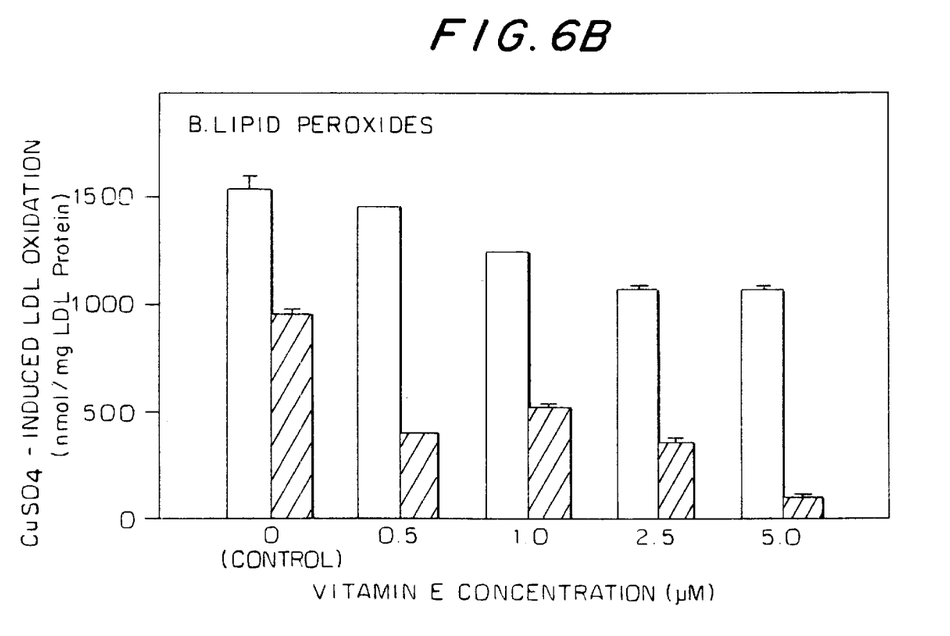
Figure 7A:
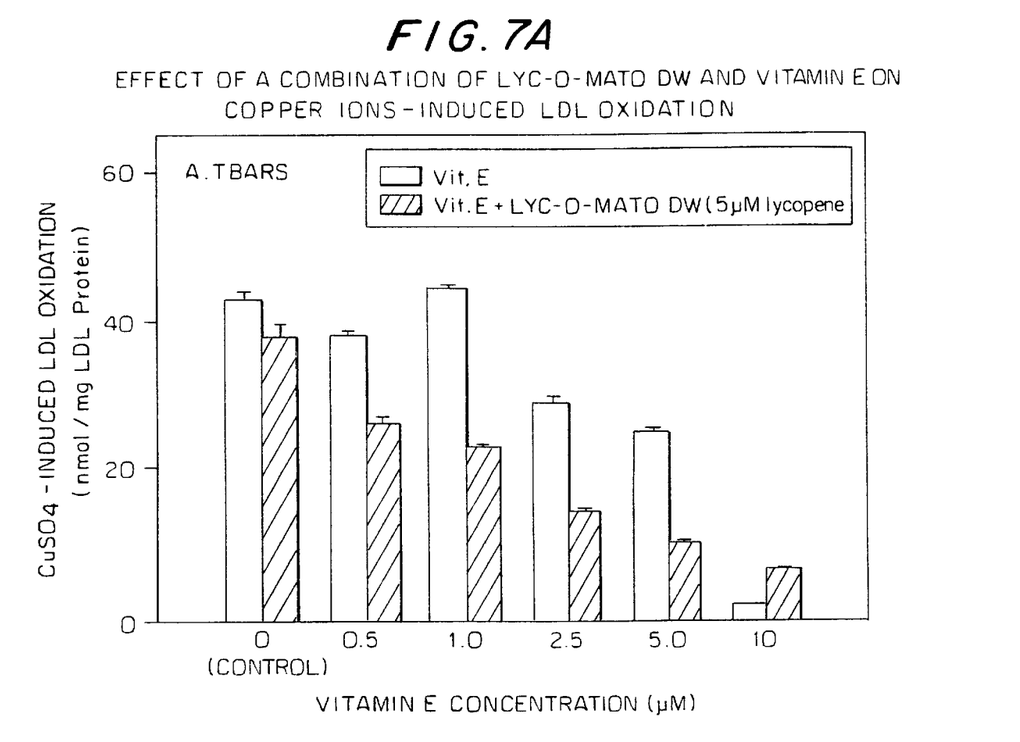
Figure 7B:
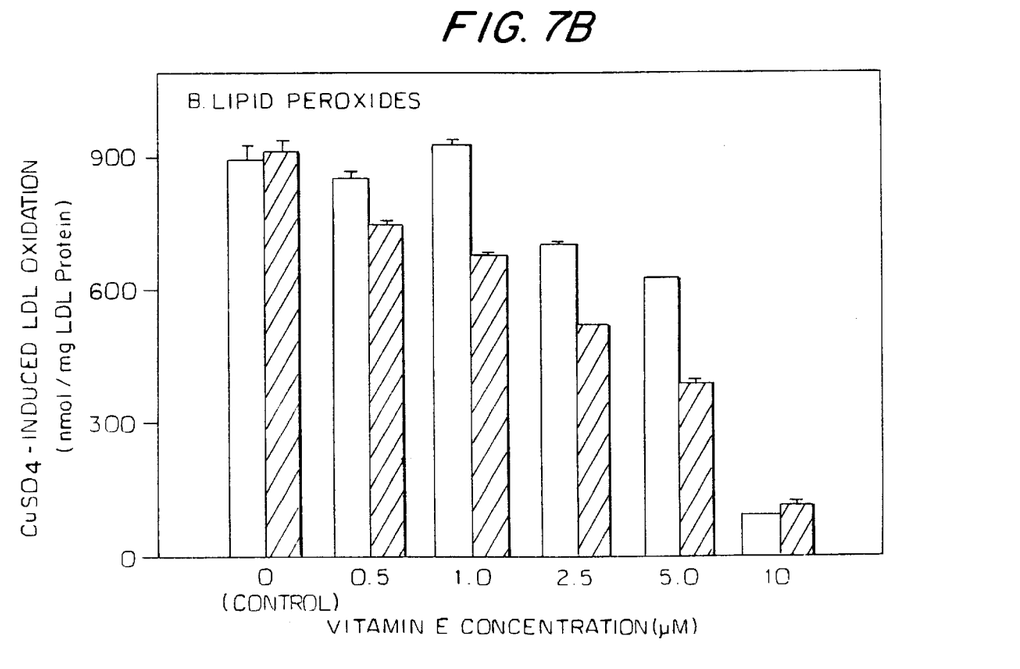

The antioxidative effect of a combination of vitamin E with lycopene against LDL oxidation, was assessed is a manner illustrated by FIGS. 5 to 7, in which the degree of inhibition of LDL oxidation by individual anti-oxidants is shown in the ordinate.

The tests hereinbefore described show that when vitamin E and lycopene are added together to LDL during copper-induced oxidation, a synergistic effect occurs. This synergistic inhibitory effect on LDL oxidation, is believed to be probably related to the contribution of vitamin E and lycopene to different antioxidative mechanisms. Whereas vitamin E is a chain breaking agent and acts as a free radicals scavenger, lycopene is a potent free radical scavenger as well as an oxygen quencher. Therefore, administration of a combination of these two antioxidants with synergistic inhibitory effects on LDL oxidation, such as vitamin E and lycopene, appears to be beneficial over the administration of individual antioxidants separately. This is further evidenced by the inhibitory effect on LDL oxidation of tomato's oleoresin, which contains a combination of antioxidants.

In some cases as published in the literature, vitamin E alone does not efficiently lower the LDL oxidation. Nevertheless, when lycopene or the oleoresin of tomatoes is added to the vitamin E, a marked synergistic lowering of the LDL oxidation occurs.

EXAMPLES

General

FIG. 1: Vitamin E dose dependent inhibition Of $CuSO_4$-induced LDL oxidation as measured by TBARS (A) or lipid peroxide (B) formation. Vitamin E is dissolved in tetrahydrofuran and the $IC_{50}$ for the inhibition of TBARS and lipid peroxides formation is 6 μM and 6.5 μM, respectively.

Figure 2A:
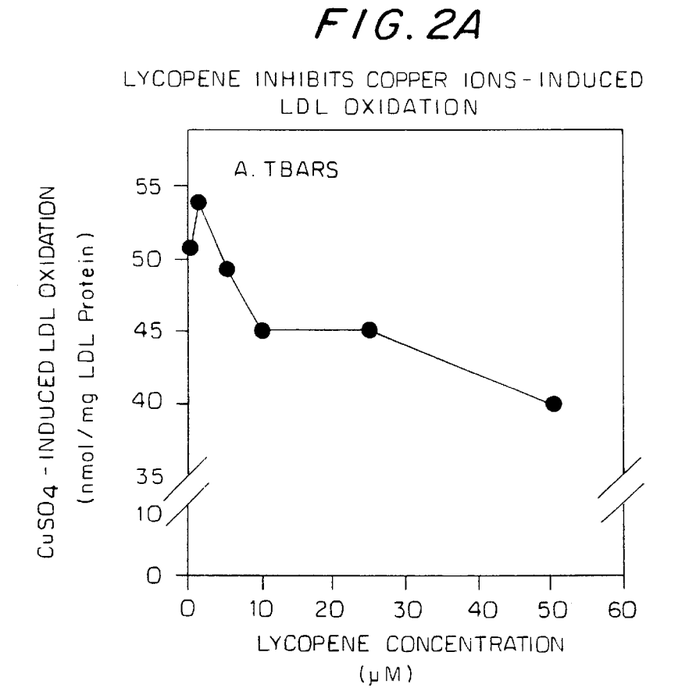
Figure 2B:
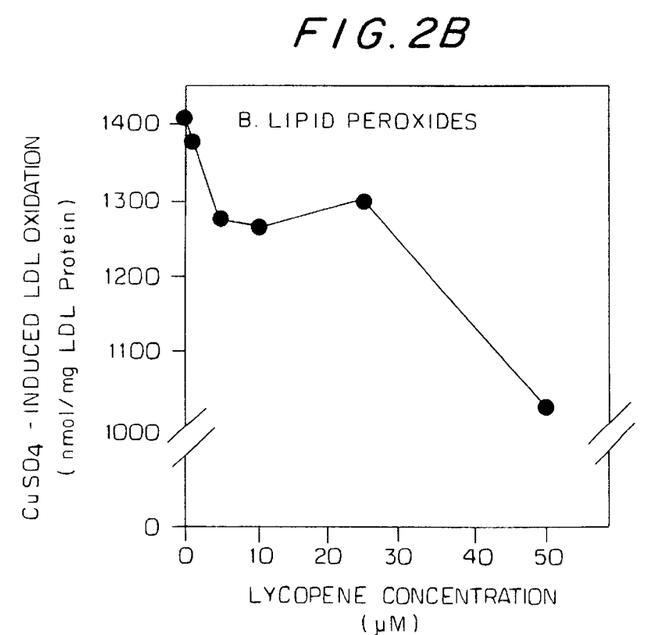

FIG. 2: Crystalline lycopene inhibition of copper-ions induced LDL oxidation. The maximal concentration used (50 μM) did not achieve 50% inhibition, neither of TBARS nor of lipid peroxides formation.

FIG. 3: LYC-O-MATO (6%) (where LYC-O-MATO is Lycored Natural Products Industries Ltd trade name for natural tomato oleoresin) inhibition of copper ions-induced LDL oxidation. The $IC_{50}$ for the inhibition of TBARS is 7.8 μM. The maximal concentration used (12 μM did not achieve 50% inhibition of lipid peroxides formation.

FIG. 4: Inhibition of copper ions-induced LDL oxidation of LYC-O-MATO (6%), which does not contain vitamin E {the vitamin E was extracted out and the material is designated as LYC-O-MATO (DW)}. The $IC_{50}$ for the inhibition of TBARS is 7.8 μM. The maximal concentration used (12 μM did not achieve 50% inhibition of lipid peroxides formation FIG. 5: Shows the results of Table 1.

FIG. 6: Shows the synergistic effect of vitamin E and LYC-O-MATO.

FIG. 7: Shows the synergistic effect of vitamin E and vitamin E extracted LYC-O-MATO.

The 1% naturally occurring vitamin E concentrates of tomato oleoresin is equal to 0.213 μM vitamin E where said oleoresin contains 6% lycopene. Thus the true concentration of vitamin E in FIG. 6 is what is listed plus 0.213 μM. FIG. 5 gives data using crystalline lycopene which does not contain any vitamin E. Similarly, for FIG. 7 which used tomato oleoresin where the vitamin E and other waxes were removed.

Example 1

The Synergistic effects of a combination of vitamin E and crystalline lycopene on copper ions-induced LDL oxidation was studied. Details are shown in Table 1, affording the individual components of the Colby Equation used to calculate synergism as follows:

$$A+B-(AB/100)=\text{Expected Control}$$

where

A=Percent control of vitamin E alone

B=Percent control of lycopene alone and $$\text{synergism}=I_F/I_E$$

where $I_F$=Actual Control in Percent $I_E$=Expected Control in Percent and synergism is proven if the ratio of $I_F/I_E$ is significantly greater than 1. The results are shown in Table 1 and FIG. 5.

Example 2

Following the method of Example 1, the synergistic effect of vitamin E and LYC-O-MATO (lycopene 6%) were determined. Results are shown in Table 1 and FIG. 6.

Example 3

Following the method of Example 1, the synergistic effect of vitamin E and vitamin E extracted LYC-O-MATO (lycopene 6%) were determined. Results are shown in Table 1 and FIG. 7.

TABLE 1

DATA (%) FROM EXPERIMERNTS 1–3 FITTED TO THE COLBY EQUATION.

| Experiment | [a]A | [a]B | $I_E$ | $I_F$ (TBARS) | $I_F$ (LIPIDS) | $I_F/I_E$ (TBARS) | $I_F/I_E$ (LIPIDS) |
|---|---|---|---|---|---|---|---|
| [b]1 | 0 | 0 | 0 | 36 | 18 | infinite | infinite |
| [c]2 | 0 | [d]42 [e]32 | [d]42 [e]32 | 68 | 49 | 1.62 | 1.53 |
| [f]3 | 0 | [d]12 [e]0 | [d]12 [e]0 | 45 | 25 | 3.75 | infinite |

[a]A = vitamin E;
[a]B = lycopene.
[b]1 μM A & 1 μM B
[c]1 μM A & 6 μM B
[d]inhibition of TBARS
[e]inhibition of lipid peroxides
[f]1 μM A & 5 μM B While embodiments of the invention and experimental data have been described by way of illustration, it should be understood that the invention is not limited thereto and may be carried out with many modifications, vairations and adaptations, without departing from its spirit or exceeding the scope of the claims

What is claimed is:

1. A synergistic pharmaceutical or dietary composition which comprises synergistic effective amounts of lycopene and vitamin E.

2. A composition in accordance with claim 1 wherein the lycopene is selected from the group consisting of lycopene from tomato oleoresin, algal, fermented, fungal, genetically modified organisms (GMO), synthetic lycopene and mixtures thereof.

3. A composition in accordance with claim 1 wherein the concentration of vitamin E is in the range of 0.025 $\mu$M to 50 $\mu$M.

4. A composition in accordance with claim 1 wherein the concentration of lycopene is in the range of 0.025 $\mu$M to 50 $\mu$M.

5. A composition in accordance with claim 3 wherein the molar ratio of lycopene to vitamin E is 1:400 to 10:1.

6. A composition in accordance with claim 1 wherein the composition contains a compound selected from the group consisting of dietary components, additives, excipients, binding agents, coatings, preservatives and mixtures thereof.

7. A composition in accordance with claim 1 wherein the lycopene and vitamin E mixture is contained in a dosage form selected from the group consisting of tablets, caplets, vegecaps and hard shell gelatin capsules.

8. A method for arresting the progression of atherosclerosis comprising synergistic effective amounts of administering to a subject in need thereof a synergistic composition containing lycopene and vitamin E.

9. A method in accordance with claim 8 wherein the lycopene is selected from the group consisting of lycopene from tomato, algal, fermented, fungal, genetically modified organisms (GMO), synthetic lycopene and mixtures thereof.

10. A method in accordance with claim 8 wherein the vitamin E concentration is in the range of 0.025 $\mu$M to 50 $\mu$M.

11. A method in accordance with claim 8 wherein the concentration of lycopene is in the range of 0.025 $\mu$M to 50 $\mu$M.

12. A method in accordance with claim 8 wherein the molar ratio of lycopene to vitamin E is 1:400 to 10:1.

13. A method in accordance with claim 8 wherein the composition contains a compound selected from the group consisting of dietary components, additives, excipients, binding agents, coatings, preservatives and mixtures thereof.

14. A method in accordance with claim 8 wherein the lycopene and vitamin E mixture is contained in a dosage form selected from the group consisting of tablets, caplets, vegecaps and hard shell gelatin capsules.

15. A method for blocking the oxidation of LDL in serum which comprises synergistic effective amounts of contacting the serum with a synergistic composition which comprises lycopene and vitamin E.

16. A method in accordance with claim 15 wherein the lycopene is selected from the group consisting of lycopene from tomato, algal, fermented, fungal, genetically modified organisms (GMO), synthetic lycopene and mixtures thereof.

17. A method in accordance with claim 15 wherein vitamin E concentration is in the range of 0.025 $\mu$M to 50 $\mu$M.

18. A method in accordance with claim 15 wherein the concentration of lycopene is in the range of 0.025 $\mu$M to 50 $\mu$M and most 0.5 $\mu$M.

19. A method in accordance with claim 17 wherein the molar ratio of lycopene to vitamin E is 1:400 to 10:1.

20. A method in accordance with claim 15 wherein the composition contains a compound selected from the group consisting of dietary components, additives, excipients, binding agents, coatings, preservatives, and mixtures thereof.

21. A method in accordance with claim 15 wherein the lycopene and vitamin E mixture is contained in a dosage form selected from the group consisting of tablets, caplets, vegecaps and hard shell gelatin capsules.

22. The method of claim 8 wherein the vitamin E concentration is 0.5 $\mu$M to 5 $\mu$M, the concentration of lycopene is 0.5 $\mu$M to 10 $\mu$M, and the molar ratio of lycopene to vitamin E is 1:80 to 5:1.

* * * * *